(12) United States Patent
Hirohara et al.

(10) Patent No.: US 6,809,065 B2
(45) Date of Patent: Oct. 26, 2004

(54) HERBICIDE CONTAINING SUBSTITUTED PYRAZOLE DERIVATIVE AS ACTIVE INGREDIENT

(75) Inventors: Yoji Hirohara, Tsukuba (JP); Eiji Ikuta, Tsukuba (JP); Takuo Kimura, Tsukuba (JP)

(73) Assignee: SDS Biotech K.K., Tokyo (JP)

( * ) Notice: Subject to any disclaimer, the term of this patent is extended or adjusted under 35 U.S.C. 154(b) by 0 days.

(21) Appl. No.: 10/380,400
(22) PCT Filed: Jul. 11, 2002
(86) PCT No.: PCT/JP02/07058
  § 371 (c)(1),
  (2), (4) Date: Mar. 12, 2003
(87) PCT Pub. No.: WO03/005825
  PCT Pub. Date: Jan. 23, 2003

(65) Prior Publication Data
  US 2004/0033898 A1 Feb. 19, 2004

(30) Foreign Application Priority Data
  Jul. 13, 2001 (JP) .............................. 2001-214479

(51) Int. Cl.$^7$ .............................................. A01N 43/56
(52) U.S. Cl. ..................... 504/156; 504/280; 504/282
(58) Field of Search .............................. 504/156, 280, 504/282

(56) References Cited

FOREIGN PATENT DOCUMENTS

| EP | 0 945 437 A1 | 9/1999 |
|---|---|---|
| JP | (1998) 10-168063 A | 6/1998 |

OTHER PUBLICATIONS

Farm Chemicals Handbook '97 (catalog), 1997, vol. 83, Meister Publishing Company, Willoughby, Ohio.
Shibuya Index (Index of Pesticides), 8$^{th}$ Ed., 1999, Shibuya Index Research Group, Tokyo, Japan.
The Pesticide Manual, 12$^{th}$ Ed., 2000, The British Crop Protection Council, Surrey, UK.
Herbicide Research Conspectus (Hakuyu–sha), 1982, no English translation.

*Primary Examiner*—S. Mark Clardy
(74) *Attorney, Agent, or Firm*—Webb Ziesenheim Logsdon Orkin & Hanson, P.C.

(57) ABSTRACT

A herbicide composition containing a substituted pyrazole derivative represented by the formula (I) set forth below as an active ingredient is disclosed, more particularly, a herbicide composition having a wide herbicidal spectrum, applicable in a small dosage with sufficient safety to certain important crops. The herbicide composition of the invention containing the substituted pyrazole derivative represented by the formula (I) as an active ingredient has a wide herbicidal spectrum, exerts an excellent herbicidal effect even in a small dose, and shows sufficient safety with respect to a number of important crops, such as rice, wheat and soybeans.

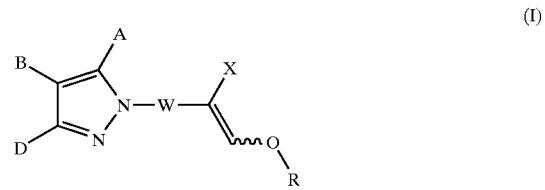

(I)

3 Claims, No Drawings

HERBICIDE CONTAINING SUBSTITUTED PYRAZOLE DERIVATIVE AS ACTIVE INGREDIENT

BACKGROUND OF THE INVENTION

1. Field of the Invention

The present invention relates to a substituted pyrazole derivative useful as a herbicide and to a herbicide composition containing the substituted pyrazole derivative as an active ingredient. More particularly, the invention relates to a herbicide composition containing as an active ingredient a substituted pyrazole derivative represented by the following formula (I), which has a wide herbicidal spectrum, can be applied in a small dose, shows sufficient safety to certain important crops and is useful in fields of chemical industry and agriculture, particularly in a field of production of agricultural chemicals.

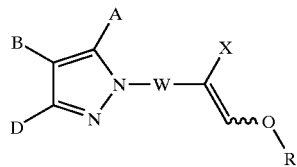

(I)

2. Description of the Prior Art

In cultivation of important crops such as wheat, corn, soybean and rice, a great number of herbicides are employed at present. However, there are many species of weeds to be controlled, and emergence of the weeds lasts over a long period of time. Therefore, most of the herbicides have a problem that their herbicidal activity, herbicidal spectrum, residual effectiveness and crop selectivity are not always satisfactory.

On this account, development of a novel herbicide composition exerting an excellent herbicidal effect even when applied in a small dose, having a wide herbicidal spectrum and showing sufficient safety to certain important crops has been desired.

Under such circumstances as mentioned above, the present inventors have made various studies, and as a result, they have found that a substituted pyrazole derivative represented by the above formula (I) has a wide herbicidal spectrum and exerts an excellent herbicidal effect and that a herbicide composition containing the substituted pyrazole derivative as an active ingredient exerts an excellent herbicidal effect even when it is applied in a small dose and shows sufficient safety to some importance crops. Based on the finding, the present invention has been accomplished.

In addition, it is also known that substituted pyrazole derivatives have fungicidal activity, and processes for synthesizing such derivatives are described in Japanese Patent Laid-Open Publication No. 168063/1998 and European Patent No. 0945437A1.

In the above publications, however, there is no description of the herbicidal activity of the substituted pyrazole derivatives at all, and also in the prior art, it has not been found that the substituted pyrazole has herbicidal activity.

SUMMARY OF THE INVENTION

It is an object of the present invention to provide a herbicide composition containing a substituted pyrazole derivative represented by the following formula (I) as an active ingredient, namely, a herbicide composition having a wide herbicidal spectrum, exerting an excellent herbicidal effect even when applied in a small dose and showing sufficient safety to some important crops.

The summary of the present invention is as follows.

(1) The herbicide composition according to the invention contains, as an active ingredient, one or more substituted pyrazole derivatives represented by the following formula (1):

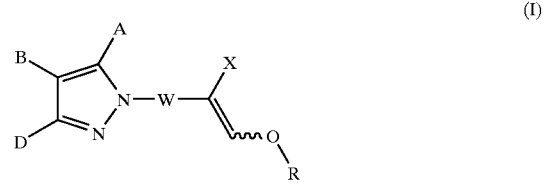

(I)

wherein X is $R^1OOC$, $R^1HNOC$, $R^1R^1NOC$, a cyano group or a 5-membered or 6-membered aromatic heterocyclic group, W is an alkylene group of 1 to 3 carbon atoms or $NR^1$, R is a lower alkyl group of 1 to 4 carbon atoms or a lower haloalkyl group of 1 to 4 carbon atoms, A, B and D may be the same or different and are each a hydrogen atom, a halogen atom or a group selected from the group consisting of $R^1$, $R^1O$, $R^1S$, $R^1SO$, $R^1SO_2$, $(R^1)_2N$, $R^1OOC$, $R^1OR^2$, $R^1ON=CH$, a cyano group, a nitro group, a lower alkenyl group of 2 to 4 carbon atoms, a lower alkynyl group of 2 to 4 carbon atoms, a cycloalkyl group of 3 to 7 carbon atoms, Ph, $PhCH_2$, PhO, $PhCH_2O$, $PhOR^2$, PhS, $PhCH_2S$, $PhSR^2$, $PhCH_2ON=CH$, Naph and Het, with the proviso that there is no case where A, B and D are hydrogen atoms at the same time and there is no case where A, B and D are aromatic groups or aromatic heterocyclic groups at the same time, $R^1$ is a lower alkyl group of 1 to 4 carbon atoms or a lower haloalkyl group of 1 to 4 carbon atoms, $R^2$ is a lower alkylene group of 1 to 4 carbon atoms, Ph is an unsubstituted or substituted phenyl group, Naph is an unsubstituted or substituted naphthyl group, and Het is an unsubstituted or substituted, 5-membered or 6-membered aromatic heterocyclic group.

(2) The herbicide composition according to the invention preferably contains as an active ingredient a substituted pyrazole derivative of the formula (I) wherein X is $R^1OOC$, W is a methylene group or an ethylene group, R is a methyl group, A and B are each a hydrogen atom, a halogen atom, $R^1$ or $R^1S$, and D is an unsubstituted or substituted phenyl group ($R^1$ is a lower alkyl group of 1 to 4 carbon atoms or a lower haloalkyl group of 1 to 4 carbon atoms).

(3) The substituted pyrazole derivative contained in the herbicide composition described in the above (1) is preferably at least one compound selected from the group consisting of the compounds No. 1 to 47 enumerated in the later-described Table 1.

(4) The substituted pyrazole derivative contained in the herbicide composition described in the above (1) is more preferably a substituted pyrazole derivative represented by the formula (I):

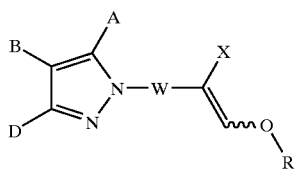

wherein X is $R^1OOC$, $R^1HNOC$ or $R^1R^1NOC$,

W is a lower alkylene group of 1 to 3 carbon atoms,

R is a lower alkyl group of 1 to 4 carbon atoms,

A and B are each a hydrogen atom, a halogen atom, $R^1$ or $R^1S$,

D is a phenyl group, a naphthyl group or a 5-membered or 6-membered aromatic heterocyclic group (these groups may be unsubstituted or may have a substituent), and $R^1$ is a lower alkyl group of 1 to 4 carbon atoms or a lower haloalkyl group of 1 to 4 carbon atoms.

DETAILED DESCRIPTION OF THE PREFERRED EMBODIMENTS

The herbicide according to the invention is described in detail hereinafter.

Substituted Pyrazole Derivatives

The substituted pyrazole derivative that is an active ingredient of the herbicide of the invention is represented by the following formula (I).

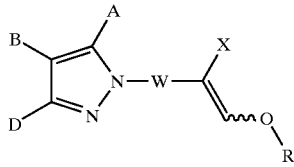

In the formula (I), X is $R^1OOC$, $R^1HNOC$, $R^1R^1NOC$, a cyano group or a 5-membered or 6-membered aromatic heterocyclic group. $R^1$ is a lower alkyl group of 1 to 4 carbon atoms or a lower haloalkyl group of 1 to 4 carbon atoms, and these groups may be straight-chain or branched. The haloalkyl group means an alkyl group substituted with one or more halogen atoms which are the same or different.

Examples of $R^1OOC$ include methoxycarbonyl group, ethoxycarbonyl group, propoxycarbonyl group and butoxycarbonyl group. Of these, methoxycarbonyl group is preferable.

Examples of $R^1HNOC$ include methylaminocarbonyl group and ethylaminocarbonyl group. Examples of $R^1R^1NOC$ include dimethylaminocarbonyl group, diethylaminocarbonyl group and ethylmethylcarbonyl group. Of these, methylaminocarbonyl group is preferable.

The 5-membered or 6-membered aromatic heterocyclic group is a 5-membered or 6-membered aromatic heterocyclic compound residue containing N, O or S atom as a cyclic atom, and examples of such groups include 2-pyridyl group, 3-pyridyl group, 4-pyridyl group, 2-furyl group, 3-furyl group, 2-thienyl group and 3-thienyl group.

In the formula (I), W is an alkylene group of 1 to 3 carbon atoms or $NR^1$, and examples of such groups include methylene group, ethylene group, trimethylene group, methylamino group and ethylamino group. Of these, methylene group is preferable.

In the formula (I), R is a lower alkyl group of 1 to 4 carbon atoms or a lower haloalkyl group of 1 to 4 carbon atoms and may be straight-chain or branched. Examples of such groups include methyl group, fluoromethyl group and difluoromethyl group. Of these, methyl group is preferable.

In the formula (I), A, B and D may be the same or different and are each a hydrogen atom, a halogen atom or a group selected from the group consisting of $R^1$, $R^1O$, $R^1S$, $R^1SO$, $R^1SO_2$, $(R^1)_2N$, $R^1OOC$, $R^1OR^2$, $R^1ON=CH$, a cyano group, a nitro group, a lower alkenyl group of 2 to 4 carbon atoms, a lower alkynyl group of 2 to 4 carbon atoms, a cycloalkyl group of 3 to 7 carbon atoms, Ph, $PhCH_2$, PhO, $PhCH_2O$, $PhOR^2$, PhS, $PhCH_2S$, $PhSR^2$, $PhCH_2ON=CH$, Naph and Het, but there is no case where A, B and D are hydrogen atoms at the same time, and there is no case where A, B and D are aromatic groups or aromatic heterocyclic groups at the same time.

$R^1$ is the same group as described above, $R^2$ is a lower alkylene group of 1 to 4 carbon atoms, Ph is an unsubstituted or substituted phenyl group, NapH is an unsubstituted or substituted naphthyl group, and Het is an unsubstituted or substituted, 5-membered or 6-memebered aromatic heterocyclic group.

Examples of the halogen atoms reperesented by A, B and D include fluorine atom, chlorine atom, bromine atom and iodine atom. Examples of $R^1$ include methyl group, ethyl group, propyl group, butyl group, fluoromethyl group, difluoromethyl group and their isomeric groups. Examples of $R^2$ include methylene group, ethylene group, trimethylene group, tetramethylene group and their isomeric groups.

Examples of $R^1O$ include methoxy group, ethoxy group, propoxy group and butoxy group. Of these, methoxy group is preferable.

Examples of $R^1S$ include methylthio group, ethylthio group, propylthio group and butylthio group. Of these, methylthio group is preferable.

Examples of $R^1SO$ include methylsulfinyl group, ethylsulfinyl group, propylsulfinyl group and butylsulfinyl group. Of these, methylsulfinyl group is preferable.

Examples of $R^1SO_2$ include methylsulfonyl group, ethylsulfonyl group, propylsulfonyl group and butylsulfonyl group. Of these, methylsulfonyl group is preferable.

Examples of $(R^1)_2N$ include dimethylamino group, diethylamino group, dipropylamino group, dibutylamino group and ethylmethylamino group.

Examples of $R^1OOC$ include methoxycarbonyl group, ethoxycarbonyl group, propoxycarbonyl group and butoxycarbonyl group. Of these, methoxycarbonyl group is preferable.

Examples of $R^1OR^2$ include methoxymethyl group, ethoxymethyl group, propoxymethyl group and butoxymethyl group.

Examples of $R^1ON=CH$ include methoxyiminomethyl group.

The lower alkenyl group of 2 to 4 carbon atoms may be straight-chain or branched, and examples of such groups include vinyl group, propenyl group, butenyl group and their isomeric groups.

The lower alkynyl group of 2 to 4 carbon atoms may be straight-chain or branched, and examples of such groups include ethynyl group, propynyl group, butynyl group and their isomeric groups.

Examples of the cycloalkyl groups of 3 to 7 carbon atoms include cyclopropyl group, cyclobutyl group, cyclopentyl group, cyclohexyl group and cycloheptyl group. Of these, cyclopropyl group is preferable.

Ph represented by A, B and D is a phenyl group, a 1- to 5-substituted phenyl group substituted with a halogen atom or a group selected from the group consisting of $R^1$, $R^1O$, $R^1S$, $R^1SO$, $R^1SO_2$, $(R^1)_2N$, $R^1OOC$, $R^1OR^2$, $R^1ON=CH$, a cyano group, a nitro group, a lower alkenyl group of 2 to 4 carbon atoms, a lower alkynyl group of 2 to 4 carbon atoms and a cycloalkyl group of 3 to 7 carbon atoms, or a 1-substituted phenyl group substituted with a group selected from the group consisting of Ph, $PhCH_2$, PhO, $PhCH_2O$, $PhCH_2ON=CR^1$, PhCO and Het—O.

Het is a 5-membered or 6-membered aromatic heterocyclic group, or a 5-membered or 6-membered aromatic heterocyclic group having a cyclic ring wherein two of substituents $R^1$ and/or $R^1O$ are present at the vicinal positions to form the cyclic structure together with the benzene ring. Examples of such groups include 2-pyridyl group, 3-pyridyl group, 4-pyridyl group, 2-furyl group, 3-furyl group, 2-thienyl group, 3-thienyl group, 1,3-benzodioxole-4-yl group, 2,2-dimethyl-1,3-benzodioxole-4-yl group and 2,2-difluoro-1,3-benzodioxole-4-yl group.

Naph represented by A, B and D is a naphthyl group or a 1- or 2-substituted naphthyl group substituted with a halogen atom, $R^1$ or $R^1O$.

Het represented by A, B and D may be a 1- to 4-substituted 5-membered or 1- to 4-substituted 6-membered aromatic heterocyclic group substituted with an alkyl group of 1 to 4 carbon atoms or a halogen atom, other than the above Het group. Examples of such groups include 2-methyl-6-pyridyl group, 3,5-dimethyl-2-furyl group, 3,5-dimethyl-2-thienyl group, N-methyl-3-pyrrolyl group and 2,4-dimethyl-5-thiazoyl group.

Preferred examples of the groups represented by A, B and D include phenyl group, methylphenyl group, chlorophenyl group, dichlorophenyl group, 3-[1-(chlorobenzyloxyimino)-ethyl]phenyl group, 3-(benzyloxy)phenyl group, 3-(methylbenzyloxy)phenyl group, 3-(chlorobenzyloxy) phenyl group, 3-(cyanobenzyloxy)phenyl group, 3-(dimethylbenzyloxy)phenyl group, 3-(dichlorobenzyloxy) phenyl group, 3-(pyridylmethoxy)phenyl group, 3-(benzoyloxy)phenyl group, 3-(chlorobenzoyloxy)phenyl group, 3-(6-chloropyrimidine-4-yloxy)phenyl group, 3-(6-methoxypyrimidine-4-yloxy)phenyl group, 3-[6-(2-methylphenoxy)-pyrimidine-4-yloxy]phenyl group, [6-(2-cyanophenoxy)pyrimidine-4-yloxy]phenyl group, 3-(6-chloro-5-nitropyrimidine-4-yloxy)phenyl group, 3-(2-benzothiazolyloxy)phenyl group, benzyl group, phenoxymethyl group, methylphenoxymethyl group, phenylthiomethyl group, methylphenylthiomethyl group, 1-phenoxyethyl group, 1-(methylphenoxy)ethyl group, 1-phenylthioethyl group, 1-(methylphenylthio)ethyl group, 1,3-benzodioxole-4-yl group, 2,2-dimethyl-1,3-benzodioxole-4-yl group, 2,2-difluoro-1,3-benzodioxole-4-yl group, phenoxy group, 2-methylphenoxy group, 3-methylphenoxy group, 4-methylphenoxy group, 2-chlorophenoxy group, 3-chlorophenoxy group, 4-chlorophenoxy group, 2-trifluoromethylphenoxy group, 2,5-dimethylphenoxy group, 2,5-dichlorophenoxy group, 2chloro-5-trifluoromethylphenoxy group, phenylthio group, 2-methylphenylthio group, 3-methylphenylthio group, 4-methylphenylthio group, 2-chlorophenylthio group, 3-chlorophenylthio group, 4-chlorophenylthio group, 2-trifluoromethylphenylthio group, 2,5-dimethylphenylthio group, 2,5-dichlorophenylthio group, 2-chloro-5-trifluoromethylphenylthio group, benzyloxy group, 2-methylbenzyloxy group, 3-methylbenzyloxy group, 4-methylbenzyloxy group, 2-chlorobenzyloxy group, 3-chlorobenzyloxy group, 4-chlorobenzyloxy group, 2-trifluoromethylbenzyloxy group, 2,5-dimethylbenzyloxy group, 2,5-dichlorobenzyloxy group, 2-chloro-5-trifluoromethylbenzyloxy group, benzylthio group, 2-methylbenzylthio group, 3-methylbenzylthio group, 4-methylbenzylthio group, 2-chlorobenzylthio group, 3-chlorobenzylthio group, 4-chlorobenzylthio group, 2-trifluoromethylbenzylthio group, 2,5-dimethylbenzylthio group, 2,5-dicholobenzylthio group, 2-chloro-5-trifluoromethylbenzylthio group, benzyloxyiminomethyl group, 2-methylbenzyloxyiminomethyl group, 3-methylbenzyloxyiminomethyl group and 4-methylbenzyloxyiminomethyl group.

Specific examples of the substituted pyrazole derivatives represented by the formula (I) include those enumerated in Table 1, but the substituted pyrazole derivatives employable in the invention are not restricted to those examples. The compound numbers in the table are referred to also in the later-described working examples. In the table, Me denotes a methyl group, Et denotes an ethyl group, Pr denotes a propyl group, and Ph denotes an unsubstituted phenyl group (only in Table 1).

Physical property values of the compounds enumerated in Table 1 are set forth in Table 2.

TABLE 1

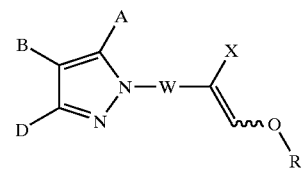

| Compound No. | A | B | D | W | X | R |
|---|---|---|---|---|---|---|
| 1 | H | H | Ph | $CH_2$ | $CO_2Me$ | Me |
| 2 | Me | H | Ph | $CH_2$ | $CO_2Me$ | Me |
| 3 | Me | H | 3-Me—Ph | $CH_2$ | $CO_2Me$ | Me |
| 4 | Me | H | 2-Cl—Ph | $CH_2$ | $CO_2Me$ | Me |
| 5 | Me | H | 2,5-(Me)$_2$—Ph | $CH_2$ | $CO_2Me$ | Me |
| 6 | Me | H | 2,3-(Cl)$_2$—Ph | $CH_2$ | $CO_2Me$ | Me |
| 7 | Me | H | 2,4-(Cl)$_2$—Ph | $CH_2$ | $CO_2Me$ | Me |
| 8 | Me | H | 2,5-(Cl)$_2$—Ph | $CH_2$ | $CO_2Me$ | Me |
| 9 | Me | H | 2,6-(Cl)$_2$—Ph | $CH_2$ | $CO_2Me$ | Me |
| 10 | Me | H | 3,4-(Cl)$_2$—Ph | $CH_2$ | $CO_2Me$ | Me |
| 11 | Me | H | 3,5-(Cl)$_2$—Ph | $CH_2$ | $CO_2Me$ | Me |
| 12 | Me | Cl | Ph | $CH_2$ | $CO_2Me$ | Me |
| 13 | H | Me | Ph | $CH_2$ | $CO_2Me$ | Me |
| 14 | H | Me | 4-F—Ph | $CH_2$ | $CO_2Me$ | Me |
| 15 | H | Cl | Ph | $CH_2$ | $CO_2Me$ | Me |
| 16 | H | Cl | 3-OMe—Ph | $CH_2$ | $CO_2Me$ | Me |
| 17 | Me | Cl | 3-Me—Ph | $CH_2$ | $CO_2Me$ | Me |
| 18 | Me | Cl | 2-Cl—Ph | $CH_2$ | $CO_2Me$ | Me |
| 19 | Me | Cl | 2,5-(Me)$_2$—Ph | $CH_2$ | $CO_2Me$ | Me |
| 20 | Me | Cl | 2,3-(Cl)$_2$—Ph | $CH_2$ | $CO_2Me$ | Me |
| 21 | Me | Cl | 2,4-(Cl)$_2$—Ph | $CH_2$ | $CO_2Me$ | Me |
| 22 | Me | Cl | 2,5-(Cl)$_2$—Ph | $CH_2$ | $CO_2Me$ | Me |
| 23 | Me | Cl | 2,6-(Cl)$_2$—Ph | $CH_2$ | $CO_2Me$ | Me |
| 24 | Me | Cl | 3,4-(Cl)$_2$—Ph | $CH_2$ | $CO_2Me$ | Me |
| 25 | Me | Cl | 3,5-(Cl)$_2$—Ph | $CH_2$ | $CO_2Me$ | Me |
| 26 | Me | Br | 3-Me—Ph | $CH_2$ | $CO_2Me$ | Me |
| 27 | Me | Br | 2-Cl—Ph | $CH_2$ | $CO_2Me$ | Me |
| 28 | Me | Br | 2,5-(Me)$_2$—Ph | $CH_2$ | $CO_2Me$ | Me |
| 29 | Me | Br | 2,3-(Cl)$_2$—Ph | $CH_2$ | $CO_2Me$ | Me |
| 30 | Me | Br | 2,4-(Cl)$_2$—Ph | $CH_2$ | $CO_2Me$ | Me |
| 31 | Me | Br | 2,5-(Cl)$_2$—Ph | $CH_2$ | $CO_2Me$ | Me |

TABLE 1-continued

| Compound No. | A | B | D | W | X | R |
|---|---|---|---|---|---|---|
| 32 | Me | Br | 3,5-(Cl)₂—Ph | CH₂ | CO₂Me | Me |
| 33 | Me | Me | Ph | CH₂ | CO₂Me | Me |
| 34 | Me | Me | 3-Cl—Ph | CH₂ | CO₂Me | Me |
| 35 | Me | Me | 4-Cl—Ph | CH₂ | CO₂Me | Me |
| 36 | Et | H | Ph | CH₂ | CO₂Me | Me |
| 37 | SMe | H | Ph | CH₂ | CO₂Me | Me |
| 38 | SMe | H | 3-Cl—Ph | CH₂ | CO₂Me | Me |
| 39 | Et | Cl | Ph | CH₂ | CO₂Me | Me |
| 40 | Pr | Cl | 3-Cl—Ph | CH₂ | CO₂Me | Me |
| 41 | SMe | Cl | Ph | CH₂ | CO₂Me | Me |
| 42 | SMe | Cl | 3-Cl—Ph | CH₂ | CO₂Me | Me |
| 43 | Et | Br | Ph | CH₂ | CO₂Me | Me |
| 44 | SMe | Br | Ph | CH₂ | CO₂Me | Me |
| 45 | Cl | Me | Ph | CH₂ | CO₂Me | Me |
| 46 | Br | Me | Ph | CH₂ | CO₂Me | Me |
| 47 | H | Me | Ph | C₂H₄ | CO₂Me | Me |

TABLE 2

| Compound No. | Physical properties | δ value (ppm, solvent: CDCl₃, internal standard substance; TMS) |
|---|---|---|
| 1 | oil | 3.55(3H, S), 3.92(3H, S), 5.02(2H, S), 6.50(1H, d, J=4.5 Hz), 7.20~7.95(7H, m) |
| 2 | oil | 2.36(3H, s), 3.69(3H, s), 3.91(3H, s), 4.88(2H, s), 6.23(1H, s), 7.10~7.90(6H, m) |
| 3 | mp 68~70° C. | |
| 4 | mp 91~92° C. | |
| 5 | oil | 2.29(3H, s), 2.37(3H, s), 3.70(3H, s), 3.90(3H, s), 4.89(2H, s), 6.08(1H, s), 6.80~7.60(4H, m) |
| 6 | oil | 2.39(3H, s), 3.69(3H, s), 3.89(3H, s), 4.90(2H, s), 6.47(1H, s), 7.00~7.80(4H, m) |
| 7 | mp 97~99° C. | |
| 8 | oil | 2.39(3H, s), 3.70(3H, s), 3.92(3H, s), 4.90(2H, s), 6.51(1H, s), 7.00~7.90(4H, m) |
| 9 | mp 121~123° C. | |
| 10 | mp 74~76° C. | |
| 11 | mp 114~116° C. | |
| 12 | mp 69~71° C. | |
| 13 | oil | 2.19(3H, s), 3.74(3H, s), 3.93(3H, s), 4.96(2H, s), 7.20~7.93(7H, m) |
| 14 | oil | 2.19(3H, s), 3.73(3H, s), 3.82(3H, s), 4.81(2H, s), 6.80~7.84(6H, m) |
| 15 | oil | 3.16(2H, s), 3.88(3H, s), 4.91(2H, s), 7.16~7.95(7H, m) |
| 16 | oil | 3.65(3H, s), 3.88(3H, s), 3.92(3H, s), 5.02(2H, s)6.77~7.58(5H, m) |
| 17 | mp 70~72° C. | |
| 18 | oil | 2.10(3H, s), 2.27(3H, s), 3.76(3H, s), 3.83(3H, s), 4.80(2H, s), 7.10~7.80(6H, m) |
| 19 | oil | 2.24(3H, s), 2.30(3H, s), 2.35(3H, s), 3.70(3H, s), 3.89(3H, s), 4.90(2H, s), 6.80~7.60(4H, m) |
| 20 | oil | 2.36(3H, s), 3.70(3H, s), 3.90(3H, s), 4.90(2H, s), 7.10~7.60(4H, m) |
| 21 | oil | 2.36(3H, s), 3.70(3H, s), 3.90(3H, s), 4.90(2H, s), 7.10~7.60(4H, m) |
| 22 | oil | 2.33(3H, s), 3.64(3H, s), 3.38(3H, s), 4.90(2H, s), 7.17~7.41(4H, m) |
| 23 | mp 107~108° C. | |
| 24 | mp 115~117° C. | |
| 25 | mp 98~110° C. | |
| 26 | oil | 2.47(6H, s), 3.67(3H, s), 3.86(3H, s), 4.88(2H, s), 7.00~7.80(4H, m) |
| 27 | oil | 2.16(3H, s), 2.38(3H, s), 3.70(3H, s), 3.89(3H, s), 4.95(2H, s), 7.05~7.60(5H, m) |
| 28 | oil | 2.22(3H, s), 2.30(3H, s), 2.37(3H, s), 3.70(3H, s), 3.89(3H, s), 4.92(2H, s), 6.90~7.60(4H, m) |
| 29 | oil | 2.35(3H, s), 3.66(3H, s), 3.84(3H, s), 4.90(2H, s), 7.05~7.60(4H, m) |
| 30 | oil | 2.37(3H, s), 3.70(3H, s), 3.89(3H, s), 4.93(2H, s), 7.10~7.70(4H, m) |
| 31 | oil | 2.38(3H, s), 3.70(3H, s), 3.90(3H, s), 4.94(2H, s), 7.10~7.60(4H, m) |
| 32 | mp 102~105° C. | |
| 33 | oil | 2.10(3H, s), 2.27(3H, s), 3.70(3H, s), 3.90(3H, s), 4.88(2H, s), 7.00~7.80(6H, m) |
| 34 | mp 98~100° C. | |
| 35 | oil | 2.05(3H, s), 2.25(3H, s), 3.65(3H, s), 3.86(3H, s), 4.83(2H, s), 7.10~7.70(5H, m) |
| 36 | oil | 1.30(3H, t, J=7.5 Hz), 2.75(2H, q, J=7.5 Hz), 3.68(3H, s), 3.89(3H, s), 4.88(2H, s), 6.27(1H, s), 7.00~7.90(6H,m) |
| 37 | oil | 2.48(3H, s), 3.71(3H, s), 3.90(3H, s), 5.07(2H, s), 6.55(1H, s), 7.10~7.90(6H, m) |
| 38 | oil | 2.47(3H, s), 3.71(3H, s), 3.92(3H, s), 5.06(2H, s), 6.52(1H, s), 7.10~7.80(5H, m) |
| 39 | oil | 1.21(3H, t, J=7.7 Hz), 2.81(2H, q, J=7.7 Hz), 3.64(3H, s), 3.84(3H, s), 4.85(2H, s), 7.10~8.00(6H, m) |
| 40 | oil | 0.89~1.95(5H, m), 3.69(3H, s), 3.89(3H, s), 5.03(2H, s), 7.17~7.40(2H, m), 7.54(1H, s), 7.64~7.81(2H, m) |
| 41 | oil | 2.41(3H, s), 3.68(3H, s), 3.87(3H, s), 5.13(2H, s), 7.20~8.00(6H, m) |
| 42 | oil | 2.43(3H, s), 3.70(3H, s), 3.91(3H, s), 5.15(2H, s), 7.20~8.00(5H, m) |
| 43 | oil | 1.19(3H, t, J=7.6 Hz), 2.82(2H, q, J=7.6 Hz), 3.65(3H, s), 3.82(3H, s), 4.87(2H, s), 7.10~8.00(6H, m) |
| 44 | oil | 2.42(3H, s), 3.70(3H, s), 3.88(3H, s), 5.18(2H, s), 7.20~8.00(6H, m) |
| 45 | resin | 1.89(3H, s), 3.70(3H, s), 3.88(3H, s), 4.64(2H, s), 7.10~8.10(6H, m) |
| 46 | resin | 2.15(3H, s), 3.75(3H, s), 3.97(3H, s), 5.29(2H, s), 7.10~8.00(6H, m) |
| 47 | oil | 2.20(3H, s), 2.78(2H, t, J=6.3 Hz), 3.66(3H, s), 3.70(3H, s), 4.17(2H, t, J=6.3 Hz), 7.16~7.77(7H, m) |

Preparation of Substituted Pyrazole Derivatives

The substituted pyrazole derivative represented by the formula (I) can be prepared in accordance with the processes described in the aforesaid publications (Japanese Patent Laid-Open Publication No. 168063/1998, European Patent No. 0945437A1). For example, a substituted pyrazole derivative of the formula (I) wherein X is $R^1OOC$, W is alkylene of 1 to 3 carbon atoms, R is lower alkyl of 1 to 4 carbon atoms, and D is Ph is favorably prepared by reacting an alkanoic acid ester derivative represented by the following formula (II) (wherein n is 1 to 3) (i.e., acetic acid ester derivative, propionic acid ester derivative or butanoic acid ester derivative) with a formylating agent in the presence of a base and a solvent, followed by the reaction with an alkylating agent in the presence of a base.

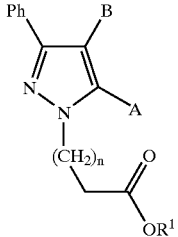

(II)

In the reaction of the alkanoic acid ester represented by the formula (II) with the formylating agent, formic acid esters and formic acid amides are used as the formylating agent. As the base, sodium hydride, alkyllithiums, lithium amides and the like are used.

With regard to the amounts of the agents used in the reaction, the formylating agent is used in an amount of about 1 to 10 equivalents and the base is used in an amount of 1 to 2 equivalents, based on 1 equivalent of the alcanoic acid ester derivative represented by the formula (II). In the above reaction, solvents, such as ethers and acid amides, are usually used.

In the reaction with the alkylating agent, alkyl halides and sulfuric acid esters are used as the alkylating agent. As the base, tertiary amines such as pyridine, inorganic bases such as sodium hydride, and the like are used.

With regard to the amounts of the agents used in the reaction, the alkylating agent is used in an amount of about 1 to 2 equivalents and the base is used in an amount of about 1 to 2 equivalents, based on 1 equivalent of the formylated compound. In the above reaction, solvents, such as ethers, acid amides and ketones, are usually used. After the reaction, the reaction mixture may be post-treated by a conventional method, and if necessary, purification is carried out, whereby the desired substituted pyrazole derivative is obtained.

The alkanoic acid ester derivative represented by the formula (II) is obtained by reacting a pyrazole derivative represented by the following formula (III):

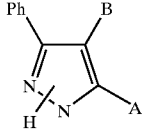

(III)

wherein A and B represent the same as the above defined symbols respectively.

with a haloacetic acid ester, a halopropionic acid ester or a halobutanoic acid ester represented by the following formula (IV):

(IV)

wherein Z is a halogen atom, $R^1$ is a lower alkyl group of 1 to 4 carbon atoms, and n is 0, 1 or 2, in the presence of a base.

Details of the process for preparing the pyrazole derivative represented by the formula (III) are as described in the aforesaid publications.

Herbicide Compositions Containing Substituted Pyrazole Derivative as Active Ingredient The herbicide composition according to the invention is characterized by containing the above-mentioned substituted pyrazole derivative as an active ingredient. The composition exerts an excellent herbicidal effect even in a small dose, with a wide herbicidal spectrum, showing sufficient safety to certain important crops.

This is attributable to the properties of the substituted pyrazole derivative, an active ingredient of the herbicide composition of the invention. The herbicidal spectrum of the substituted pyrazole derivative and the crop selectivity thereof are described below in detail.

Herbicidal Activity of Substituted Pyrazole Derivative (A) Herbicidal Spectrum (A1) Herbicidal Spectrum in an Upland Field In any treatment among soil treatment, soil incorporation treatment and foliage treatment, the substituted pyrazole derivative for use in the invention has high herbicidal activity as an upland field or non-crop land herbicide even in a small dose against various species of upland field weeds, for example, broad leaf weeds, specifically, Solanaceae weeds, such as *Solanum nigrum* and *Datura stramonium*, Malvaceae weeds, such as *Abutilon theophrasti* and *Sida spinosa*, Convolvulaceae weeds, such as Ipomoea spps. (e.g., *Ipomoea purpurea*) and Calystegia spps., Amaranthaceae weeds, such as *Amaranthus lividus* and *Amaranthus retroflexus*, Compositae weeds, such as *Xanthium pensylvanicum, Ambrosia artemisiaefolia, Helianthus annuus, Galinsoga ciliata, Cirsium arvense, Senecio vulgaris, Erigeron annus* and *Matricaria inodora*, Cruciferae weeds, such as *Rorippa indica, Sinapis arvensis* and *Capsella Bursapastoris*, Polygonaceae weeds, such as *Polygonum Blumei* and *Polygonum convolvulus*, Portulacaceae weeds, such as *Portulaca oleracea*, Chenopodiaceae weeds, such as *Chenopodium album, Chenopodium ficifolium* and *Kochia scoparia*, Caryophyllaceae weeds, such as *Stellaria media*, Scrophulariaceae weeds, such as *Veronica persica*, Commelinaceae weeds, such as *Commelina communis*, Labiatae weeds, such as *Lamium amplexicaule* and *Lamium purpureum*, Euphorbiaceae weeds, such as *Euphorbia supina* and *Euphorbia maculata*, Rubiaceae weeds, such as *Galium spurium* and *Rubia akane*, Violaceae weeds, such as *viola mandshurica*, and Laguminosae weeds, such as *Sesbania exaltata* and *Cassia obtusifolia*; and other weeds, specifically, Gramineous weeds, such as *Sorgham bicolor, Panicum dichotomiflorum, Sorghum halepense, Echinochloa crus-galli var. crus-galli, Echindchloa crus-galli var. praticola, Echinochloa utilis, Digitaria adscendens*, Avenafatua, *Eleusine indica, Setaria viridis, Alopecurus aegualis* and *Poa annua*, and Cyperaceous weeds, such as *Cyperus rotundus* (*Cyperus esculentus*).

Further, weeds over a wide range, such as those which emerge in mowed field, non-cultivation land, land under perennial crops, pasture, lawn, railway side, vacant lot, forest, farm load, levee and other non-crop lands, can be removed.

(A2) Herbicidal Spectrum in an Paddy Field

In any treatment of water-logged soil treatment and foliage treatment, the substituted pyrazole derivative for use in the invention has high herbicidal activity as a paddy field herbicide even in a small dose against various species of paddy field weeds, specifically, Alismataceae weeds, such as *Alisma canaliculatum, Sagittaria trifolia* and *Sagittaria pygmaea*, Cyperaceous weeds, such as *Cyperus difformis, Cyperus serotinus, Scirpus juncoides, Eleocharis kuroguwai* and *Eleocharis acicularis*, Scrophulariaceae weeds, such as *Lindernia pyxidaria*, Pontederiaceae weeds, such as *Monochoria vaginalis*, Potamogetonaceae weeds, such as *Potamogeton distinctus*, Umbelliferae weeds, such as *Oenanthe javanica*, Lythraeae weeds, such as *Rotala indica* and *Ammannia multiflora*, Elantinaceae weeds, such as *Elatine triandra*, and Graminaceous weeds, such as *Echinochloa oryzicola, Echinochloa crus-galli var. formosensis* and *Echinochloa crus-galli var. crus-galli*.

(A3) Effect on Aquatic Plants

The substituted pyrazole derivative for use in the invention exerts an effect on algae, such as blue-green algae, and aquatic weeds, such as *Eichhornia crassipes*, which emerge in creeks, canals, lakes, marshes, ponds, etc.

(B) Crop Selectivity (B1) Crop Selectivity in an Upland Field

The substituted pyrazole derivative for use in the invention shows high safety to main crops, such as *Oryza sativa, Triticum aestivum, Hordeum vulgare, Sorghum bicolor, Arachis hypogaea, Zea mays, Glycine max*, Gossypium spp. and *Beat vulgaris*, and garden crops, such as flowers, ornamental plants and vegetable crops.

(B2) Crop Selectivity (Paddy Rice)

The substituted pyrazole derivative for use in the invention does not pose a significant chemical hazard to transplantation paddy rice or direct-sowing paddy rice.

(B3) Crop Selectivity (Lawn Grass)

The substituted pyrazole derivative for use in the invention shows high safety to lawn grasses, such as Japanese lawn grass and Western lawn grass.

Ingredients of the Herbicide Composition

The herbicide composition of the invention contains, as an active ingredient, the substituted pyrazole derivative having such a wide herbicidal spectrum and such a crop selectivity as described above. Although the content of the substituted pyrazole derivative can be changed according to the conditions such as formulation of the herbicide composition and application method thereof and is not specifically restricted, it is in the range of usually about 0.01 to 90% by weight.

The herbicide composition of the invention may contain one or more kinds of the substituted pyrazole derivatives as active ingredients.

The herbicide composition of the invention may further contain, in addition to the substituted pyrazole derivative, one or plural plant protecting agents, such as fungicides, insecticides, herbicides, nematicides, acaricides, bactericides, chemical injury decreasing agents, plant growth regulators, fertilizers and soil improvers, as mixed chemicals.

By the addition of such other ingredients, particularly other herbicidal active ingredients (referred to as "other herbicides" hereinafter), it becomes possible to reduce the total dose of the herbicide composition. Moreover, besides labor-saving, widening of a herbicidal spectrum and much higher herbicidal effect can be expected owing to the synergistic action of the mixed chemicals. The herbicide composition may contain plural kinds of other herbicides at the same time.

Examples of the other herbicides include those described in a catalog of Farm Chemical Handbook (Meister Publishing Company) (1997), SHIBUYA INDEX (8th edition) (1999), The Pesticide Manual (British crop protection council) 12th edition (2000), and Herbicide research conspectus (Hakuyu-sha), such as atrazine, cyanazine, dimethametryn, metribuzin, prometryn, simazine, simetryn, chlortoluron, diuron, daimuron, fluometuron, isoproturon, linuron, methabenzthiazuron, amicarbazone, bromoxynil, ioxynil, ethalfluralin, pendimethalin, trifluralin, acifluorfen, acifluorfen-sodium, bifenox, chlomethoxynil, fomesafen, lactofen, oxadiazon, oxadiargyl, oxyfluorfen, carfentrazone-ethyl, flumiclorac-pentyl, flumioxazine, fluthiacet-methyl, sulfentrazone, thidiazimin, azafenidin, pyraflufen-ethyl, cinidon-ethyl, difenzoquat, diquat, paraquat, 2,4-D, 2,4-DB, DCPA, MCPA, MCPB, clomeprop, clopyralid, dicamba, dithiopyr, fluroxypyr, mecoprop, naploanilide, phenothiol, quinclorac, triclopyr, thiazopyr, acetochlor, alachlor, butachlor, diethatyl-ethyl, metolachlor, pretilachlor, propachlor, bensulfuron-methyl, chlorsulfuron, chlorimuron-ethyl, halosulfuron-methyl, metsulfuron-methyl, nicosulfuron, primisulfuron-methyl, pyrazosulfuron-ethyl, sulfometuron-ethyl, thifensulfuron-methyl, triasulfuron, tribenuron-methyl, oxasulfuron, azimsulfuron, cloransulam-methyl, cyclosulfamuron, flumetsulam, florasulam, flupyrsulfuron, flazasulfuron, imazosulfuron, metosulam, diclosulam, prosulfuron, rimsulfuron, triflusulfuron-methyl, ethoxysulfuron, sulfosulfuron, flucarbazone-sodium, procarbazone-sodium (MKH-6561), imazamethabenz-methyl), imazapyr, imazaquin, imazethapyr, imazameth, imazamox, bispyribac-sodium, pyriminobac-methyl, pyrithiobac-sodium, alloxydim-sodium, clethodim, sethoxydim, tralkoxydim, tepraloxydim, profoxydim (BAS-625H), diclofop-methyl, fenoxaprop-ethyl, fenoxaprop-p-ethyl, fluazifop-butyl, fluazifop-p-butyl, haloxyfop-methyl, quizalofop-p-ethyl, cyhalofop-butyl, clodinafop-propargyl, benzofenap, clomazone, diflufenican, norflurazone, pyrazolate, pyrazoxyfen, picolinafen, beflubutamid, flurtamone, isoxaflutole, sulcotrione, benzobicyclon, mesotrione, glufosinate-ammonium, glyphosate, bentazone, benthiocarb, bromobutide, butamifos, butylate, dimepiperate, dimethenamid, DSMA, EPTC, esprocarb, isoxaben, mefenacet, molinate, MSMA, piperophos, pyributicarb, prosulfocarb, propanil, pyridate, triallate, cafenstrol, flupoxam, flufenacet, diflufenzopyr, triaziflam, pentoxazone, indanofan, metobenzuron, oxaziclomefone and fentrazamide.

Although the mixing ratio between the substituted pyrazole derivative and other herbicides in the herbicide composition of the invention varies depending upon the types of active ingredients of other herbicides, etc., it is preferably in the range of usually 1:0.01 to 1:10, by weight.

Formulation

There is no specific limitation on the formulation of the herbicide composition of the invention, as far as the composition contains the substituted pyrazole derivative as an active ingredient. For example, in the practical application as a herbicide, the substituted pyrazole derivative may be used just as it is, but by the addition of additives generally used for formulating, such as carriers, surface active agents, dispersants and adjuvants, the herbicide composition can be used as any of generally adoptable formulations of agricultural chemicals, such as wettable powders, granules, powders, emulsions, water-soluble powders, suspensions and flowables.

Examples of the solid carriers or diluents include plant substances, fibrous materials, synthetic plastic powders, clays (e.g., kaolin, bentonite, terra abla), talc or inorganic materials (pumice, powdered sulfur), and chemical fertilizers. Examples of the liquid carriers or diluents include water, alcohols, ketones, ethers, aromatic hydrocarbons, aliphatic hydrocarbons, esters, nitrites, amides (N,N-dimethylformamide, dimethyl sulfoxide), and halogenated hydrocarbons.

Examples of the surface active agents include alkylsulfuric acid esters, alkyl sulfonates, polyethylene glycol ethers and polyhydric alcohol esters. Examples of the spreaders or the dispersants include casein, gelatin, starch, caboxymethyl cellulose, gum arabic, alginic acid, lignin, bentonite, polyvinyl alcohol, pine oil, molasses and agar.

Examples of the stabilizers include isopropylphosphate mixture, tricresyl phosphate, tall oil, epoxy oil, surface active agents, fatty acids and the esters thereof.

The concentration of the active ingredient in the herbicide composition of the invention can be variously changed according to the formulation as described above, and in case of wettable powders, the active ingredient concentration is desirable to be in the range of preferably 5 to 90% by weight, more preferably 10 to 85% by weight. In case of emulsions, the active ingredient concentration is desirable to be in the range of preferably 3 to 70% by weight, more preferably 5 to 60% by weight, and in case of granules, the active ingredient concentration is desirable to be in the range of preferably 0.01 to 50% by weight, more preferably 0.05 to 40% by weight.

Also when the herbicide composition of the invention contains the aforesaid other herbicides, the formulation is not specifically restricted, and for example, it is possible that the substituted pyrazole derivative and the active ingredient of other herbicides are each previously mixed with a solid carrier, a liquid carrier, a surface active agent or other formulation adjuvants to prepare an emulsion, a wettable powder, a suspension, a water-soluble granule, a water-soluble powder, an aqueous solution, a water-dispersible granule or the like, followed by mixing. It is also possible that the substituted pyrazole derivative is mixed with other herbicides and then the admixture is mixed with a solid carrier, a liquid carrier, a surface active agent or other formulation adjuvants to prepare an emulsion, a wettable powder, a suspension, a granule, a concentrated emulsion, a water-dispersible granule or the like. In the resulting formulation, the substituted pyrazole derivative and other herbicides are desirably contained at the total amount of preferably 0.5 to 80% by weight, more preferably 1.5 to 70% by weight.

Application Method

When the herbicide composition of the invention is applied as a herbicide, plants can be directly treated with the composition by spraying, dispersing, spreading or coating. Otherwise, the soil around the plants, upland field, paddy field, lawn, etc. can be treated with the composition by application or incorporation.

In case of, for example, a wettable powder or an emulsion, the powder or the emulsion is diluted with water to give a suspension or a dilute emulsion of a prescribed concentration, and the suspension or the dilute emulsion can be sprayed or incorporated before or after sprouting of the objective weeds. In case of a granule, the granule can be directly applied or incorporated as such before or after sprouting of the objective weeds. When the herbicide composition of the invention is practically applied as a herbicide, the composition can be used in such a proper amount that the amount of the active ingredient becomes usually not less than 0.1 g based per hectare.

When the herbicide composition of the invention is practically used as a herbicide, the amount of the composition used is desired to be in the range of usually 10 g to 8000 g, preferably 10 g to 2000 g per hectare, though it varies with the meteorological conditions, formulation types, application times, application methods, soil conditions, objective crops, weeds to be controlled, etc. In case of an emulsion, a wettable powder, a suspension, a concentrated emulsion, a water-dispersible granule, a liquid or the like, it is preferable to dilute a given amount of the formulation with usually 10 to 100 liters of water or water optionally containing adjuvants such as a spreader, prior to application. In case of a granule, a certain suspension or a certain liquid, it is preferable to apply it as such without diluting. Examples of the adjuvants include the surface active agents described above, polyoxyethylene fatty acid esters, lignin sulfonic acid salts, abietic acid salts, dinaphthylmethanedisulfonic acid salts, and vegetable oils, such as crop oil concentrate, soybean oil, corn oil, cotton seed oil and sunflower oil.

The herbicide composition of the invention containing, as an active ingredient, a substituted pyrazole derivative represented by the aforesaid formula (I) has a wide herbicidal spectrum, can be applied in a small dose and shows sufficient safety to certain important crops such as rice, wheat and soybeans.

EXAMPLE

The present invention is further described with reference to the following formulation examples and test examples, but it should be understood that the invention is in no way limited by or to those examples. In the following description, the term "part(s)" means "part(s) by weight".

As the control chemical, a compound of the following formula (V) was used.

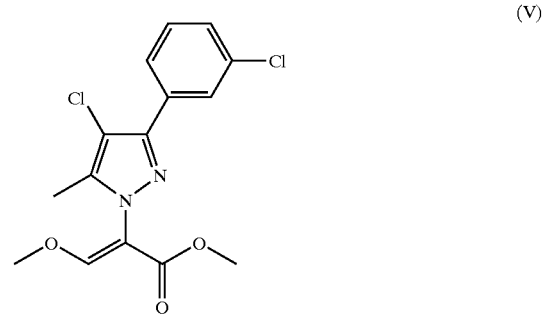

(V)

Formulation Example 1

Wettable Powder Composition

50 Parts of each compound shown in Table 2 (Compound No. 1 to 47), 20 parts of diatomaceous earth, 22 parts of clay, 3 parts of white carbon, 2 parts of lignin sulfonic acid soda and 3 parts of alkylnaphthalenesulfonic acid soda were mixed and pulverized to obtain a wettable powder composition containing 50% by weight of an active ingredient. The control chemical was subjected to the same procedures as described above to obtain a wettable powder composition.

Formulation Example 2

Granule Composition 0.35 Part of each compound shown in Table 2 (Compound No. 1 to 47), 25 parts of bentonite, 70.65 parts of talc, 2 parts of dodecylbenzenesulfonic acid soda and 2 parts of lignin sulfonic acid soda were mixed. To the mixture, about 20 parts of water was added. The resulting mixture was kneaded by a kneader, granulated by a granulator and then subjected to drying and sieving to obtain a granule composition containing 0.35% by weight of an active ingredient. The control chemical was subjected to the same procedures as described above to obtain a granule composition.

Test examples of the herbicidal effects exerted by the herbicide compositions of the invention are given below, but it should be understood that the invention is in no way limited by or to those test examples.

The test results were evaluated according to the following criteria.

Evaluation Criteria

Index: 0–5

5: herbicidal effect of not less than 90% by weight
4: herbicidal effect of not less than 70% by weight and less than 90% by weight
3: herbicidal effect of not less than 50% by weight and less than 70% by weight
2: herbicidal effect of not less than 30% by weight and less than 50% by weight
1: herbicidal effect of not less than 10% by weight and less than 30% by weight
0: herbicidal effect of not less than 0% by weight and less than 10% by weight In the above evaluation criteria, the term "herbicidal effect" means evaluation to the objective weeds, and a higher index of the evaluation criteria means higher herbicidal effect on the objective weeds. On the other hand, a lower index of the evaluation criteria for the crops means higher safety to the crops.

Test Example 1

Upland Field Foliage Treatment

A plastic pot of 130 $cm^2$ was filled with upland soil. Then, seeds of weeds, namely, *Setaria viridis, Digitaria adscendens, Chenopodium album* and *Stellaria media*, and seeds of crops, namely, soybean (*Glycine max*) and wheat (*Triticum aestivum*), were sowed and covered with soil of about 1 cm thick.

On the 14th day after the sowing, a wettable powder composition was prepared in accordance with Formulation Example 1, diluted with water in such an amount that the amount of the active ingredient became 1 kg per hectare, and then uniformly applied to the plant leaf surfaces.

On the 21st day after the application, observation and evaluation were carried out according to the aforesaid criteria.

The results are set forth in Table 3.

Test Example 2

Upland Soil Treatment

A plastic pot of 130 $cm^2$ was filled with upland soil. Then, seeds of weeds, namely, *Setaria viridis, Digitaria adscendens, Chenopodium album* and *Stellaria media,* and seeds of crops, namely, soybean (*Glycine max*) and wheat (*Triticum aestivum*), were sowed and covered with soil of about 1 cm thick.

On the next day after the sowing, a wettable powder composition was prepared in accordance with Formulation Example 1, diluted with water in such an amount that the amount of the active ingredient became 1 kg per hectare, and then uniformly applied to the soil surface.

On the 21st day after the application, observation and evaluation were carried out according to the aforesaid criteria.

The results are set forth in Table 4.

Test Example 3

Paddy Field Treatment

A plastic pot of 130 $cm^2$ was filled with paddy soil, and soil puddling was carried out to adjust the submerged depth to 4 cm. Then, seeds of *Echinochloa crusgalli, Monochoria vaginalis, Ammannia multiflora* and *Scirpus juncoides* were sowed, and rice (*Oryza sative*, variety: Koshihikari) of two-leaf period was transplanted by 2 rice plants of 1 stub per pot at a depth of 3 cm. On the 10th day after the transplantation, a wettable powder composition was prepared in accordance with Formulation Example 1, diluted with water in such an amount that the amount of the active ingredient became 1 kg per hectare, and then dropped to diffuse on the water surface.

On the 21st day after the dropping, observation and evaluation were carried out according to the aforesaid criteria.

The results are set forth in Table 5.

TABLE 3

| | Herbicidal activity | | | | | |
|---|---|---|---|---|---|---|
| Compound No. | Setaria viridis | Digitaria adscendens | Chenopodium album | Stellaria media | Glycine max | Triticum aestivum |
| 1 | 5 | 5 | 5 | 5 | 1 | 1 |
| 2 | 4 | 4 | 4 | 4 | 0 | 0 |
| 3 | 5 | 4 | 5 | 5 | 0 | 0 |
| 4 | 4 | 4 | 5 | 4 | 0 | 0 |
| 5 | 4 | 4 | 5 | 4 | 0 | 0 |
| 6 | 4 | 4 | 4 | 4 | 0 | 0 |
| 7 | 4 | 4 | 5 | 5 | 0 | 0 |
| 8 | 4 | 5 | 5 | 5 | 0 | 0 |
| 9 | 4 | 4 | 4 | 4 | 0 | 0 |
| 10 | 4 | 4 | 4 | 4 | 0 | 0 |
| 11 | 4 | 4 | 4 | 4 | 0 | 0 |
| 12 | 4 | 5 | 5 | 5 | 1 | 0 |
| 13 | 5 | 5 | 5 | 5 | 0 | 0 |
| 14 | 5 | 5 | 5 | 5 | 0 | 0 |

TABLE 3-continued

Herbicidal activity

| Compound No. | Setaria viridis | Digitaria adscendens | Chenopodium album | Stellaria media | Glycine max | Triticum aestivum |
|---|---|---|---|---|---|---|
| 15 | 5 | 5 | 5 | 5 | 1 | 0 |
| 16 | 5 | 5 | 5 | 5 | 1 | 0 |
| 17 | 5 | 4 | 5 | 5 | 0 | 0 |
| 18 | 4 | 5 | 5 | 5 | 0 | 0 |
| 19 | 4 | 5 | 5 | 4 | 0 | 0 |
| 20 | 4 | 4 | 5 | 5 | 0 | 0 |
| 21 | 4 | 5 | 5 | 5 | 1 | 0 |
| 22 | 4 | 5 | 5 | 5 | 0 | 0 |
| 23 | 4 | 4 | 4 | 5 | 0 | 0 |
| 24 | 4 | 4 | 4 | 4 | 0 | 0 |
| 25 | 4 | 4 | 4 | 4 | 0 | 0 |
| 26 | 4 | 5 | 5 | 5 | 1 | 0 |
| 27 | 4 | 5 | 5 | 5 | 0 | 0 |
| 28 | 4 | 4 | 5 | 5 | 0 | 0 |
| 29 | 4 | 5 | 5 | 5 | 1 | 1 |
| 30 | 4 | 5 | 5 | 5 | 1 | 0 |
| 31 | 5 | 5 | 5 | 5 | 1 | 1 |
| 32 | 4 | 4 | 4 | 4 | 0 | 0 |
| 33 | 4 | 5 | 5 | 5 | 0 | 0 |
| 34 | 4 | 5 | 5 | 4 | 1 | 1 |
| 35 | 4 | 4 | 4 | 4 | 0 | 0 |
| 36 | 5 | 4 | 5 | 5 | 1 | 1 |
| 37 | 4 | 4 | 5 | 5 | 0 | 0 |
| 38 | 4 | 4 | 5 | 5 | 1 | 0 |
| 39 | 4 | 4 | 5 | 5 | 1 | 0 |
| 40 | 4 | 4 | 4 | 4 | 0 | 0 |
| 41 | 4 | 4 | 4 | 4 | 0 | 0 |
| 42 | 4 | 4 | 4 | 4 | 0 | 0 |
| 43 | 4 | 4 | 5 | 5 | 0 | 0 |
| 44 | 4 | 4 | 4 | 4 | 0 | 0 |
| 45 | 4 | 4 | 5 | 5 | 1 | 0 |
| 46 | 4 | 4 | 5 | 5 | 1 | 0 |
| 47 | 3 | 3 | 4 | 4 | 0 | 0 |
| Control | 0 | 0 | 0 | 0 | 0 | 0 |

TABLE 4

Herbicidal activity

| Compound No. | Setaria viridis | Digitaria adscendens | Chenopodium album | Stellaria media | Glycine max | Triticum aestivum |
|---|---|---|---|---|---|---|
| 1 | 4 | 5 | 4 | 4 | 0 | 0 |
| 2 | 4 | 4 | 4 | 4 | 0 | 0 |
| 3 | 4 | 4 | 4 | 4 | 0 | 0 |
| 4 | 4 | 4 | 4 | 4 | 0 | 0 |
| 5 | 4 | 5 | 4 | 4 | 0 | 0 |
| 6 | 4 | 4 | 4 | 4 | 0 | 0 |
| 7 | 5 | 4 | 4 | 4 | 0 | 0 |
| 8 | 4 | 4 | 4 | 4 | 0 | 0 |
| 9 | 4 | 4 | 5 | 4 | 0 | 0 |
| 10 | 4 | 5 | 4 | 4 | 0 | 0 |
| 11 | 4 | 4 | 4 | 4 | 0 | 0 |
| 12 | 4 | 5 | 5 | 4 | 0 | 0 |
| 13 | 5 | 5 | 5 | 5 | 0 | 0 |
| 14 | 5 | 5 | 5 | 5 | 0 | 0 |
| 15 | 5 | 5 | 5 | 5 | 0 | 0 |
| 16 | 5 | 5 | 4 | 5 | 0 | 0 |
| 17 | 4 | 4 | 4 | 4 | 0 | 0 |
| 18 | 4 | 5 | 5 | 5 | 0 | 0 |
| 19 | 4 | 5 | 4 | 5 | 0 | 0 |
| 20 | 4 | 4 | 5 | 4 | 0 | 0 |
| 21 | 4 | 4 | 4 | 4 | 0 | 0 |
| 22 | 5 | 5 | 5 | 5 | 0 | 0 |
| 23 | 4 | 4 | 4 | 4 | 0 | 0 |
| 24 | 4 | 4 | 4 | 4 | 0 | 0 |
| 25 | 4 | 4 | 4 | 4 | 0 | 0 |
| 26 | 4 | 4 | 4 | 4 | 0 | 0 |
| 27 | 4 | 5 | 4 | 5 | 0 | 0 |
| 28 | 4 | 4 | 4 | 4 | 0 | 0 |
| 29 | 4 | 4 | 4 | 4 | 0 | 0 |
| 30 | 5 | 5 | 4 | 4 | 0 | 0 |
| 31 | 5 | 5 | 5 | 5 | 0 | 0 |

TABLE 4-continued

| | Herbicidal activity | | | | | |
|---|---|---|---|---|---|---|
| Compound No. | Setaria viridis | Digitaria adscendens | Chenopodium album | Stellaria media | Glycine max | Triticum aestivum |
| 32 | 4 | 4 | 4 | 4 | 0 | 0 |
| 33 | 4 | 4 | 4 | 4 | 0 | 0 |
| 34 | 4 | 4 | 4 | 4 | 0 | 0 |
| 35 | 4 | 4 | 4 | 4 | 0 | 0 |
| 36 | 4 | 4 | 4 | 4 | 0 | 0 |
| 37 | 5 | 5 | 4 | 5 | 0 | 0 |
| 38 | 4 | 4 | 4 | 4 | 0 | 0 |
| 39 | 4 | 4 | 4 | 4 | 0 | 0 |
| 40 | 4 | 4 | 4 | 4 | 0 | 0 |
| 41 | 4 | 4 | 4 | 4 | 0 | 0 |
| 42 | 4 | 4 | 4 | 4 | 0 | 0 |
| 43 | 4 | 4 | 4 | 4 | 0 | 0 |
| 44 | 4 | 4 | 4 | 4 | 0 | 0 |
| 45 | 4 | 4 | 4 | 4 | 0 | 0 |
| 46 | 4 | 4 | 4 | 4 | 0 | 0 |
| 47 | 4 | 4 | 4 | 3 | 0 | 0 |
| Control | 0 | 0 | 0 | 0 | 0 | 0 |

TABLE 5

| | Herbicidal activity | | | | |
|---|---|---|---|---|---|
| Compound No. | Echinochloa spp. | Scirpus juncoides | Monochoria vaginalis | Ammannia multiflora | Oryza sativa |
| 1 | 5 | 5 | 5 | 4 | 1 |
| 2 | 3 | 3 | 3 | 3 | 0 |
| 3 | 3 | 3 | 4 | 4 | 0 |
| 4 | 4 | 4 | 5 | 3 | 0 |
| 5 | P | 3 | 5 | 3 | 0 |
| 6 | 4 | 3 | 3 | 3 | 0 |
| 7 | 4 | 3 | 4 | 4 | 0 |
| 8 | 4 | 4 | 5 | 5 | 0 |
| 9 | 3 | 3 | 3 | 3 | 0 |
| 10 | 3 | 3 | 3 | 3 | 0 |
| 11 | 3 | 3 | 3 | 3 | 0 |
| 12 | 4 | 4 | 5 | 5 | 0 |
| 13 | 5 | 5 | 5 | 5 | 0 |
| 14 | 5 | 5 | 5 | 5 | 0 |
| 15 | 5 | 5 | 5 | 5 | 0 |
| 16 | 5 | 5 | 5 | 5 | 0 |
| 17 | 5 | 4 | 5 | 5 | 0 |
| 18 | 5 | 5 | 5 | 5 | 1 |
| 19 | 5 | 5 | 5 | 5 | 1 |
| 20 | 4 | 4 | 5 | 5 | 0 |
| 21 | 5 | 4 | 5 | 5 | 0 |
| 22 | 5 | 5 | 5 | 5 | 1 |
| 23 | 3 | 3 | 4 | 5 | 0 |
| 24 | 4 | 3 | 3 | 3 | 0 |
| 25 | 3 | 3 | 3 | 3 | 0 |
| 26 | 5 | 4 | 5 | 5 | 0 |
| 27 | 5 | 5 | 5 | 5 | 1 |
| 28 | 5 | 5 | 5 | 5 | 1 |
| 29 | 4 | 4 | 5 | 5 | 0 |
| 30 | 4 | 4 | 5 | 5 | 0 |
| 31 | 5 | 5 | 5 | 5 | 1 |
| 32 | 3 | 3 | 3 | 3 | 0 |
| 33 | 5 | 5 | 5 | 5 | 1 |
| 34 | 3 | 3 | 5 | 3 | 0 |
| 35 | 3 | 3 | 4 | 4 | 0 |
| 36 | 3 | 3 | 3 | 3 | 0 |
| 37 | 3 | 3 | 3 | 3 | 0 |
| 38 | 3 | 3 | 4 | 3 | 0 |
| 39 | 4 | 4 | 3 | 3 | 0 |
| 40 | 3 | 3 | 3 | 3 | 0 |
| 41 | 4 | 3 | 3 | 3 | 0 |
| 42 | 3 | 3 | 3 | 3 | 0 |
| 43 | 3 | 4 | 3 | 3 | 0 |
| 44 | 3 | 3 | 3 | 3 | 0 |
| 45 | 4 | 4 | 5 | 4 | 0 |
| 46 | 3 | 3 | 3 | 3 | 0 |
| 47 | 3 | 3 | 2 | 2 | 0 |
| Control | 0 | 0 | 0 | 0 | 0 |

What is claimed is:

1. A method of exerting a herbicidal effect on algae or weeds comprising applying a herbicide composition to algae or weeds, the herbicide composition containing, as an active ingredient, one or more substituted pyrazole derivatives represented by the following formula (I):

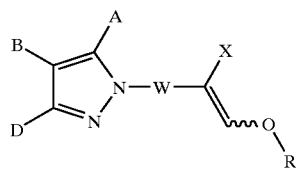

wherein X is $R^1OOC$, $R^1HNOC$, $R^1R^1NOC$, a cyano group or a 5-membered or 6-membered aromatic heterocyclic group, W is an alkylene group of 1 to 3 carbon atoms or $NR^1$, R is a lower alkyl group of 1 to 4 carbon atoms or a lower haloalkyl group of 1 to 4 carbon atoms, A, B and D may be the same or different and are each a hydrogen atom, a halogen atom or a group selected from the group consisting of $R^1$, $R^1O$, $R^1S$, $R^1SO$, $R^1SO_2$, $(R^1)_2N$, $R^1OOC$, $ROR^2$, $R^1ON=CH$, a cyano group, a nitro group, a lower alkenyl group of 2 to 4 carbon atoms, a lower alkynyl group of 2 to 4 carbon atoms, a cycloalkyl group of 3 to 7 carbon atoms, Ph, $PhCH_2$, PhO, $PhCH_2O$, $PhOR^2$, PhS, $PhCH_2S$, $PhSR^2$, $PhCH_2ON=CH$, Naph and Het, with the proviso that there is no case where A, B and D are hydrogen atoms at the same time and there is no case where A, B and D are aromatic groups or aromatic heterocyclic groups at the same time, $R^1$ is a lower alkyl group of 1 to 4 carbon atoms or a lower haloalkyl group of 1 to 4 carbon atoms, $R^2$ is a lower alkylene group of 1 to 4 carbon atoms, Ph is an unsubstituted or substituted phenyl group, Naph is an unsubstituted or substituted naphthyl group, and Het is an unsubstituted or substituted, 5-membered or 6-membered aromatic heterocyclic group.

2. The method as claimed in claim 1, wherein the substituted pyrazole derivative is a substituted pyrazole derivative of the formula (I) wherein X is $R^1OOC$, W is a methylene group or an ethylene group, R is a methyl group, A and B are each a hydrogen atom, a halogen atom, $R^1$ or $R^1S$, and D is Ph.

3. The method as claimed in claim 1, wherein the substituted pyrazole derivative represented by the formula (I) is at least one compound selected from the group consisting of:

a substituted pyrazole derivative (compound No. 1) wherein A and B are each a hydrogen atom, D is a phenyl group, W is a methylene group, X is a methoxycarbonyl group, and R is a methyl group, a substituted pyrazole derivative (compound No. 2) wherein A is a methyl group, B is a hydrogen atom, D is a phenyl group, W is a methylene group, X is a methoxycarbonyl group, and R is a methyl group, a substituted pyrazole derivative (compound No. 3) wherein A is a methyl group, B is a hydrogen atom, D is a 3-methylphenyl group, W is a methylene group, X is a methoxycarbonyl group, and R is a methyl group, a substituted pyrazole derivative (compound No. 4) wherein A is a methyl group, B is a hydrogen atom, D is a 2-chlorophenyl group, W is a methylene group, X is a methoxycarbonyl group, and R is a methyl group, a substituted pyrazole derivative (compound No. 5) wherein A is a methyl group, B is a hydrogen atom, D is a 2,5-dimethylphenyl group, W is a methylene group, X is a methoxycarbonyl group, and R is a methyl group, a substituted pyrazole derivative (compound No. 6) wherein A is a methyl group, B is a hydrogen atom, D is a 2,3-dichlorophenyl group, W is a methylene group, X is a methoxycarbonyl group, and R is a methyl group, a substituted pyrazole derivative (compound No. 7) wherein A is a methyl group, B is a hydrogen atom, D is a 2,4-dichlorophenyl group, W is a methylene group, X is a methoxycarbonyl group, and R is a methyl group, a substituted pyrazole derivative (compound No. 8) wherein A is a methyl group, B is a hydrogen atom, D is a 2,5-dichlorophenyl group, W is a methylene group, X is a methoxycarbonyl group, and R is a methyl group, a substituted pyrazole derivative (compound No. 9) wherein A is a methyl group, B is a hydrogen atom, D is a 2,6-dichlorophenyl group, W is a methylene group, X is a methoxycarbonyl group, and R is a methyl group, a substituted pyrazole derivative (compound No. 10) wherein A is a methyl group, B is a hydrogen atom, D is a 3,4-dichlorophenyl group, W is a methylene group, X is a methoxycarbonyl group, and R is a methyl group, a substituted pyrazole derivative (compound No. 11) wherein A is a methyl group, B is a hydrogen atom, D is a 3,5-dichlorophenyl group, W is a methylene group, X is a methoxycarbonyl group, and R is a methyl group, a substituted pyrazole derivative (compound No. 12) wherein A is a methyl group, B is a chlorine atom, D is a phenyl group, W is a methylene group, X is a methoxycarbonyl group, and R is a methyl group, a substituted pyrazole derivative (compound No. 13) wherein A is a hydrogen atom, B is a methyl group, D is a phenyl group, W is a methylene group, X is a methoxycarbonyl group, and R is a methyl group, a substituted pyrazole derivative (compound No. 14) wherein A is a hydrogen atom, B is a methyl group, D is a 4-fluorophenyl group, W is a methylene group, X is a methoxycarbonyl group, and R is a methyl group, a substituted pyrazole derivative (compound No. 15) wherein A is a hydrogen atom, B is a chlorine atom, D is a phenyl group, W is a methylene group, X is a methoxycarbonyl group, and R is a methyl group, a substituted pyrazole derivative (compound No. 16) wherein A is a hydrogen atom, B is a chlorine atom, D is a 3-methoxyphenyl group, W is a methylene group, X is a methoxycarbonyl group, and R is a methyl group, a substituted pyrazole derivative (compound No. 17) wherein A is a methyl group, B is a chlorine atom, D is a 3-methylphenyl group, W is a methylene group, X is a methoxycarbonyl group, and R is a methyl group, a substituted pyrazole derivative (compound No. 18) wherein A is a methyl group, B is a chlorine atom, D is a 2-chlorophenyl group, W is a methylene group, X is a methoxycarbonyl group, and R is a methyl group, a substituted pyrazole derivative (compound No. 19) wherein A is a methyl group, B is a chlorine atom, D is a 2,5-dimethylphenyl group, W is a methylene group, X is a methoxycarbonyl group, and R is a methyl group, a substituted pyrazole derivative (compound No. 20) wherein A is a methyl group, B is a chlorine atom, D is a 2,3-dichlorophenyl group, W is a methylene group, X is a methoxycarbonyl group, and R is a methyl group, a substituted pyrazole derivative (compound No. 21) wherein A is a methyl group, B is a chlorine atom, D is a 2,4-dichlorophenyl group, W is a methylene group, X is a methoxycarbonyl group, and R is a methyl group, a substituted pyrazole derivative (compound No. 22) wherein A is a methyl group, B is a chlorine atom, D is a 2,5-dichlorophenyl group, W is a methylene group, X is a methoxycarbonyl group, and R is a methyl group, a substituted pyrazole derivative (compound No. 23) wherein A is a methyl group, B is a chlorine atom, D is a 2,6-dichlorophenyl group, W is a methylene group, X is a methoxycarbonyl group, and R is a methyl group, a substituted pyrazole derivative (compound No. 24) wherein A is a methyl group, B is a chlorine atom, D is a 3,4-dichlorophenyl group, W is a methylene group, X is a methoxycarbonyl group, and R is a methyl group, a substituted pyrazole derivative (compound No. 25) wherein A is a methyl group, B is a chlorine atom, D is a 3,5-dichlorophenyl group, W is a methylene group, X is a methoxycarbonyl group, and R is a methyl group, a substituted pyrazole derivative (compound No. 26) wherein A is a methyl group, B is a bromine atom, D is a 3-methylphenyl group, W is a methylene group, X is a methoxycarbonyl group, and R is a methyl group, a substituted pyrazole derivative (compound No. 27) wherein A is a methyl group, B is a bromine atom, D is a 2-chlorophenyl group, W is a methylene group, X is a methoxycarbonyl group, and R is a methyl group, a substituted pyrazole derivative (compound No. 28) wherein A is a methyl group, B is a bromine atom, D is a 2,5-dimethylphenyl group, W is a methylene group, X is a methoxycarbonyl group, and R is a methyl group, a substituted pyrazole derivative (compound No. 29) wherein A is a methyl group, B is a bromine atom, D is a 2,3-dichlorophenyl group, W is a methylene group, X is a methoxycarbonyl group, and R is a methyl group, a substituted pyrazole derivative (compound No. 30) wherein A is a methyl group, B is a bromine atom, D is a 2,4-dichlorophenyl group, W is a methylene group, X is a methoxycarbonyl group, and R is a methyl group, a substituted pyrazole derivative (compound No. 31) wherein A is a methyl group, B is a bromine atom, D is a 2,5-dichlorophenyl group, W is a methylene group, X is a methoxycarbonyl group, and R is a methyl group, a substituted pyrazole derivative (compound No. 32) wherein A is a methyl group, B is a bromine atom, D is a 3,5-dichlorophenyl group, W is a methylene group, X is a methoxycarbonyl group, and R is a methyl group, a substituted pyrazole derivative (compound No. 33) wherein A is a methyl group, B is a methyl group, D is a phenyl group, W is a methylene group, X is a methoxycarbonyl group, and R is a methyl group, a substituted pyrazole derivative (compound No. 34) wherein A is a methyl group, B is a methyl group, D is a 3-chlorophenyl group, W is a methylene group, X is a methoxycarbonyl group, and R is a methyl group, a substituted pyrazole derivative (compound No. 35) wherein A is a methyl group, B is a methyl group, D is a 4-chlorophenyl group, W is a methylene group, X is a methoxycarbonyl group, and R is a methyl group, a substituted pyrazole derivative (compound No. 36) wherein A is an ethyl group, B is a hydrogen atom, D is a phenyl group, W is a methylene group, X is a methoxycarbonyl group, and R is a methyl group, a substituted pyrazole derivative (compound No. 37) wherein A is a methylthio group, B is a hydrogen atom, D is a phenyl group, W is a methylene group, X is a methoxycarbonyl group, and R is a methyl group, a substituted pyrazole derivative (compound No. 38) wherein A is a methylthio group, B is a hydrogen atom, D is a 3-chlorophenyl group, W is a methylene group, X is a methoxycarbonyl group, and R is a methyl group, a substituted pyrazole derivative (compound No. 39) wherein A is an ethyl group, B is a chlorine atom, D is a phenyl group, W is a methylene group, X is a methoxycarbonyl group, and R is a methyl group, a substituted pyrazole derivative (compound No. 40) wherein A is a propyl group, B is a chlorine atom, D is a 3-chlorophenyl group, W is a methylene group, X is a methoxycarbonyl group, and R is a methyl group, a substituted pyrazole derivative (compound No. 41) wherein A is a methylthio group, B is a chlorine atom, D is a phenyl group, W is a methylene group, X is a methoxycarbonyl group, and R is a methyl group, a substituted pyrazole derivative (compound No. 42) wherein A is a methylthio group, B is a chlorine atom, D is a 3-chlorophenyl group, W is a methylene group, X is a methoxycarbonyl group, and R is a methyl group, a substituted pyrazole derivative (compound No. 43) wherein A is an ethyl group, B is a bromine atom, D is a phenyl group, W is a methylene group, X is a methoxycarbonyl group, and R is a methyl group, a substituted pyrazole derivative (compound No. 44) wherein A is a methylthio group, B is a bromine atom, D is a phenyl group, W is a methylene group, X is a methoxycarbonyl group, and R is a methyl group, a substituted pyrazole derivative (compound No. 45) wherein A is a chlorine atom, B is a methyl group, D is a phenyl group, W is a methylene group, X is a methoxycarbonyl group, and R is a methyl group, a substituted pyrazole derivative (compound No. 46) wherein A is a bromine atom, B is a methyl group, D is a phenyl group, W is a methylene group, X is a methoxycarbonyl group, and R is a methyl group, and a substituted pyrazole derivative (compound No. 47) wherein A is a hydrogen atom, B is a methyl group, D is a phenyl group, W is an ethylene group, X is a methoxycarbonyl group, and R is a methyl group.

* * * * *